(12) United States Patent
Yoon et al.

(10) Patent No.: US 12,167,908 B2
(45) Date of Patent: Dec. 17, 2024

(54) DYNAMIC BIO IMPEDANCE RANGE ADJUSTMENT FOR A MEDICAL DEVICE

(71) Applicant: Medtronic, Inc., Minneapolis, MN (US)

(72) Inventors: Hyun J. Yoon, Vadnais Heights, MN (US); Jon E. Thissen, Rosemount, MN (US); Jerry D. Reiland, Coon Rapids, MN (US); Ashley L Galarneau, Eagan, MN (US)

(73) Assignee: Medtronic, Inc., Minneapolis, MN (US)

( * ) Notice: Subject to any disclaimer, the term of this patent is extended or adjusted under 35 U.S.C. 154(b) by 221 days.

(21) Appl. No.: 17/380,705

(22) Filed: Jul. 20, 2021

(65) Prior Publication Data
US 2022/0031184 A1 Feb. 3, 2022

Related U.S. Application Data

(60) Provisional application No. 63/059,562, filed on Jul. 31, 2020.

(51) Int. Cl.
*A61B 5/053* (2021.01)
*A61B 5/25* (2021.01)

(52) U.S. Cl.
CPC ............... *A61B 5/053* (2013.01); *A61B 5/25* (2021.01); *A61B 2562/0219* (2013.01)

(58) Field of Classification Search
CPC ... A61B 5/053; A61B 5/25; A61B 2562/0219; A61B 2562/162; A61B 5/686;
(Continued)

(56) References Cited

U.S. PATENT DOCUMENTS 3,971,365 A 7/1976 Smith
4,870,341 A * 9/1989 Pihl ...................... A61N 1/3931
324/600

(Continued)

FOREIGN PATENT DOCUMENTS

CN 111308206 A 6/2020
JP 2007132778 A 5/2007

OTHER PUBLICATIONS

International Search Report and Written Opinion of International Application No. PCT/US2021/042678, mailed Oct. 29, 2021, 11 pp.
(Continued)

*Primary Examiner* — Yi-Shan Yang
*Assistant Examiner* — Joseph A Tombers
(74) *Attorney, Agent, or Firm* — Shumaker & Sieffert, P.A.

(57) ABSTRACT

This disclosure is directed to devices, systems, and techniques for dynamically adjusting a bio impedance measurement range. An example device includes a plurality of electrodes. The device also includes sensing circuitry configured to sense a bio impedance and processing circuitry. The processing circuitry is configured to apply an excitation signal to the sensing circuitry and, based on the application of the excitation signal, determine a sensed bio impedance value within a bio impedance measurement range. The processing circuitry is also configured to determine whether the sensed bio impedance value is within a predetermined portion of the bio impedance measurement range for a predetermined period of time and based on the sensed bio impedance value being within the predetermined portion of the bio impedance measurement range for the predetermined period of time, adjust the excitation signal.

20 Claims, 9 Drawing Sheets

(58) Field of Classification Search
CPC ....... A61B 5/0205; A61B 5/0537; A61B 5/29; A61B 5/4875; A61B 5/6869; A61B 5/7221
See application file for complete search history.

(56) References Cited

U.S. PATENT DOCUMENTS

| | | |
|---|---|---|
| 7,092,757 B2 | 8/2006 | Larson et al. |
| 7,457,660 B2 | 11/2008 | Smith et al. |
| 8,065,001 B1 | 11/2011 | Nabutovsky et al. |
| 8,131,356 B2 | 3/2012 | Belalcazar et al. |
| 8,157,848 B2 | 4/2012 | Zhang et al. |
| 8,731,653 B2 | 5/2014 | Patterson et al. |
| 8,934,966 B2 | 1/2015 | Osawa |
| 9,591,987 B1 | 3/2017 | Liedtke |
| 9,999,397 B2 | 6/2018 | Lee et al. |
| 10,016,607 B2 | 7/2018 | Min |
| 10,120,005 B2 | 11/2018 | Cherkassky et al. |
| 2010/0113888 A1* | 5/2010 | Cho ........................ A61B 5/349 600/301 |
| 2011/0082383 A1 | 4/2011 | Cory et al. |
| 2019/0175063 A1* | 6/2019 | Groenendaal ........ A61B 5/2415 |
| 2021/0252293 A1* | 8/2021 | English ................. A61B 5/283 |

OTHER PUBLICATIONS

"Measurement Range", Sourcetronic GmbH, retrieved on Oct. 20, 2021 from https://www.sourcetronic.com/en/glossary/measurement-range/, 1 pp.

Kusche et al., "A Multichannel Real-Time Bioimpedance Measurement Device for Pulse Wave Analysis," IEEE Transactions on Biomedical Circuits and Systems, vol. 12, No. 3, Jun. 2018, 10 pp.

* cited by examiner

DYNAMIC BIO IMPEDANCE RANGE ADJUSTMENT FOR A MEDICAL DEVICE

This application claims the benefit of U.S. Provisional Patent Application No. 63/059,562, filed Jul. 31, 2020, the entire contents of which is incorporated herein by reference.

TECHNICAL FIELD

The disclosure relates generally to medical device systems and, more particularly, medical device systems configured to monitor patient parameters.

BACKGROUND

Some types of medical devices may be used to monitor one or more physiological parameters of a patient. Such medical devices may include, or may be part of a system that includes, sensors that detect signals associated with such physiological parameters. Values determined based on such signals may be used to assist in detecting changes in patient conditions, in evaluating the efficacy of a therapy, or in generally evaluating patient health.

SUMMARY

In general, the disclosure is directed to devices, systems, and techniques for using a medical device to collect bio impedance values of a patient. Bio impedance values (e.g., BioZ values) are an effective manner of monitoring patient parameters. In some examples, bio impedance values may be effective in monitoring a patient's heart failure condition. For example, bio impedance values may be used to calculate heart failure scores and monitor disease progress. However, if a patient's actual bio impedance value is out of a bio impedance measurement range of the medical device used to sense the patient's bio impedance, such as above an upper boundary limit of the bio impedance measurement range or below a lower boundary limit of the bio impedance measurement range, the measurements may be inaccurate and a clinician analyzing the measurements may be less able to monitor heart failure progression and be less able to determine the effectiveness of medical, pharmaceutical or other treatment.

According to the techniques of this disclosure, the bio impedance measurement range of a medical device may be dynamically changed to lessen the occurrence of erroneous measurements. In some examples, the medical device may periodically determine whether the measured bio impedance value is within a predetermined portion (e.g., a bottom portion or a top portion) of the bio impedance measurement range for a predetermined period of time (e.g., two or three days). Based on the measured bio impedance value being within the predetermined portion of the bio impedance measurement range for a predetermined period of time, the medical device may adjust an excitation signal, such as a current or voltage applied to sensing circuitry used to sense bio impedance. Adjusting the excitation signal applied to the sensing circuitry may change the upper boundary limit of the bio impedance measurement range, thus dynamically changing the bio impedance measurement range of the device. The adjusting of the excitation signal may be done in a manner that enlarges the bio impedance measurement range and thus moves the measured bio impedance value toward the center of the adjusted bio impedance measurement range. In this manner, the medical device may more accurately measure bio impedance values, permitting a clinician to, for example, more accurately follow the progression of heart failure of the patient.

In some examples, a device includes: a plurality of electrodes; sensing circuitry configured to sense a bio impedance; and processing circuitry configured to: apply an excitation signal to the plurality of electrodes via the sensing circuitry; based on the application of the excitation signal, determine a sensed bio impedance value within a bio impedance measurement range; determine whether the sensed bio impedance value is within a predetermined portion of the bio impedance measurement range for a predetermined period of time; and based on the sensed bio impedance value being within the predetermined portion of the bio impedance measurement range for the predetermined period of time, adjust the excitation signal, wherein adjusting the excitation signal adjusts the bio impedance measurement range.

In some examples, a method includes: applying, by processing circuitry, an excitation signal to a plurality of electrodes via sensing circuitry; determining, by the processing circuitry and based on the application of the excitation signal, a sensed bio impedance value within a bio impedance measurement range; determining, by the processing circuitry, whether the sensed bio impedance value is within a predetermined portion of the bio impedance measurement range for a predetermined period of time; and based on the sensed bio impedance value being within the predetermined portion of the bio impedance measurement range for the predetermined period of time, adjusting the excitation signal, wherein adjusting the excitation signal adjusts the bio impedance measurement range.

In some examples, a non-transitory computer-readable medium includes instructions for causing one or more processors to: apply an excitation signal to a plurality of electrodes via sensing circuitry; determine, based on the application of the excitation signal, a sensed bio impedance value within a bio impedance measurement range; determine whether the sensed bio impedance value is within a predetermined portion of the bio impedance measurement range for a predetermined period of time; and based on the sensed bio impedance value being within the predetermined portion of the bio impedance measurement range for the predetermined period of time, adjust the excitation signal, wherein adjusting the excitation signal adjusts the bio impedance measurement range.

The summary is intended to provide an overview of the subject matter described in this disclosure. It is not intended to provide an exclusive or exhaustive explanation of the systems, device, and methods described in detail within the accompanying drawings and description below. Further details of one or more examples of this disclosure are set forth in the accompanying drawings and in the description below. Other features, objects, and advantages will be apparent from the description and drawings, and from the claims.

BRIEF DESCRIPTION OF DRAWINGS

Like reference characters denote like elements throughout the description and figures.

DETAILED DESCRIPTION

Figure 1:
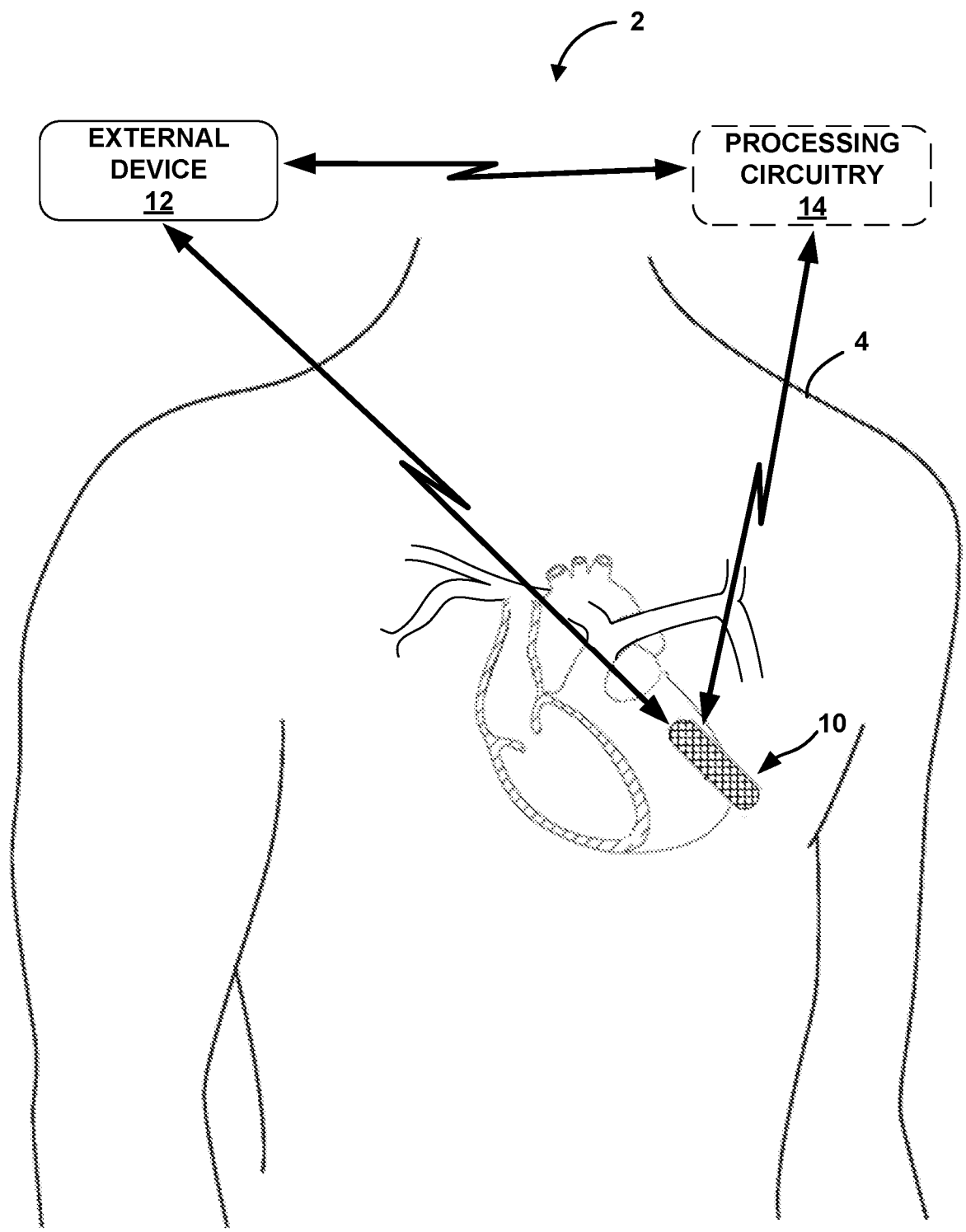
FIG. 1 illustrates the environment of an example medical device system in conjunction with a patient, in accordance with one or more techniques of this disclosure.

This disclosure describes techniques for dynamically adjusting a bio impedance measurement range of a medical device. Measuring a bio impedance value is an effective way to determine fluid content of a patient's body and to determine respiration activity of the patient, as examples. For example, a DC component of a measured bio impedance may be indicative of the fluid content in the patient's body and a relatively small AC component of a measured bio impedance may be indicative of respiration activity of the patient. Both the fluid content of a patient's body and respiration may be used individually or together as part of a calculation for a heart failure score which may provide a clinician with a manner for following the progression of heart failure in the patient.

Bio impedance may be measured by applying an excitation signal, such as a current or voltage, to sensing circuitry in an implantable medical device (IMD), delivering the excitation signal (such as a current or voltage) via a plurality of electrodes coupled to the sensing circuitry, and measuring the resulting other of current or voltage. Processing circuitry of IMD 10 may determine a bio impedance value based on the delivered excitation signal and the measured voltage or current.

The bio impedance values may be transmitted to an external device, for example on a periodic basis (such as daily) and may be used by a clinician to monitor the progression of heart failure in the patient. A given excitation signal, such as a current or voltage, establishes a respective bio impedance measurement range for which the IMD may measure a patient's bio impedance value. When implanting the IMD, a clinician may determine the appropriate excitation signal to accurately measure the patient's bio impedance. For example, the clinician may attempt to select an excitation current or voltage that would place the measured bio impedance at or near the center of the bio impedance measurement range.

If the patient later loses weight or gains weight, the measured bio impedance value may change. For example, muscle tissue is more conductive than fat tissue. Muscle tissue may have an impedance in the range of 200 ohms to 2000 ohms, while fat tissue may have an impedance in the range 1500 ohms to 5000 ohms. Thus, if a patient gains or loses weight, the tissue contacting the electrodes used to sense the patient's bio impedance value may change, causing the measured bio impedance value to change for reasons unrelated to the condition of the patient being monitored by the IMD. If the patient's health significantly changes, the measured bio impedance value may also change. Furthermore, if the IMD migrates in the patient's body so as to cause electrodes of the IMD used to sense the bio impedance value of the patient to contact different tissue in the patient, the measured bio impedance value may also change. These types of changes may move the measured bio impedance value away from the center of the bio impedance measurement range towards the top or the bottom of the bio impedance measurement range or even move the actual bio impedance value of the patient outside of the lower boundary limit or upper boundary limit of the bio impedance measurement range. For example, if the patient's actual bio impedance value is 3000 ohms and the top of the bio impedance measurement range is 2500 ohms, the IMD would measure the bio impedance value as being 2500 ohms. In this case, the IMD may not accurately measure the DC component of bio impedance indicative of fluid retention or be able measure the relatively small AC component of the bio impedance signal representative of respiration activity, as the actual bio impedance value of the patient is outside of the bio impedance measurement range. Thus, a fixed lower boundary limit and upper boundary limit of the bio impedance measurement range may work well at first, but become less effective over time.

If the lower boundary limit or the upper boundary limit of the bio impedance measurement range is incorrect (e.g., the actual bio impedance value of the patient is outside of the bio impedance measurement range or at the top or the bottom of the bio impedance measurement range), the measured bio impedance value may not be equal to the actual bio impedance value of the patient. Thus, the measured bio impedance value may be less useful to a clinician monitoring a health condition or status of the patient, such as the progression of heart failure in the patient. According to the techniques of this disclosure, a device, such as an IMD, or one or more implantable or external devices, may be used to measure the bio impedance value of a patient. The lower boundary limit and/or the upper boundary limit of the bio impedance measurement range of the device may be dynamically adjusted by adjusting an excitation signal, such as a current or voltage, in such manner as to change the bio impedance measurement range so that the measured bio impedance value of the patient is more towards the center of the bio impedance measurement range than the measured bio impedance value otherwise would be. In this manner, the IMD may relatively accurately measure bio impedance value of the patient even after the patient gains or loses weight, the patient's health situation changes significantly, or the IMD migrates within the patient's body. In some examples, the bio impedance measurement range may be adjusted automatically (e.g., without the intervention of a clinician or patient).

FIG. 1 illustrates the environment of an example medical device system 2 in conjunction with a patient 4, in accordance with one or more techniques of this disclosure. While the techniques described herein are generally described in the context of an insertable cardiac monitor, the techniques of this disclosure may be implemented in any implantable medical device configured to measure bioimpedance, such as a cardiac pacemaker and/or a defibrillator, or neurostimulator, which may be coupled to electrodes via leads. The example techniques may be used with an IMD 10, which may be in wireless communication with at least one of external device 12 and other devices not pictured in FIG. 1. Processing circuitry 14 is conceptually illustrated in FIG. 1 as separate from IMD 10 and external device 12, but may be processing circuitry of IMD 10 and/or processing circuitry of external device 12. In general, the techniques of this disclosure may be performed by processing circuitry 14 of one or more devices of a system, such as one or more devices that include sensors that provide signals, or processing circuitry of one or more devices that do not include sensors, but nevertheless analyze signals using the techniques described herein. For example, another external device (not pictured in FIG. 1) may include at least a portion of processing circuitry 14, the other external device configured for remote communication with IMD 10 and/or external device 12 via a network.

In some examples, IMD 10 is implanted outside of a thoracic cavity of patient 4 (e.g., subcutaneously in the pectoral location illustrated in FIG. 1). IMD 10 may be positioned near the sternum near or just below the level of patient 4's heart, e.g., at least partially within the cardiac silhouette. In some examples, IMD 10 takes the form of a LINQ™ Insertable Cardiac Monitor (ICM), available from Medtronic plc, of Dublin, Ireland.

Clinicians sometimes diagnose patients with medical conditions based on one or more observed physiological signals collected by physiological sensors, such as electrodes, optical sensors, chemical sensors, temperature sensors, acoustic sensors, and motion sensors. In some cases, clinicians apply non-invasive sensors to patients in order to sense one or more physiological signals while a patient is in a clinic for a medical appointment. However, in some examples, physiological markers (e.g., irregular heartbeats and long-term respiration trends) of a patient condition are rare or are difficult to observe over a relatively short period of time. As such, in these examples, a clinician may be unable to observe the physiological markers needed to diagnose a patient with a medical condition while monitoring one or more physiological signals of the patient during a medical appointment. In the example illustrated in FIG. 1, IMD 10 is implanted within patient 4 to continuously record one or more physiological signals, such as bio impedance, of patient 4 over an extended period of time.

In some examples, IMD 10 includes a plurality of electrodes. The plurality of electrodes is configured to detect signals that enable processing circuitry 14, e.g., of IMD 10, to determine current values of additional parameters associated with the cardiac and/or lung functions of patient 4. For example, the plurality of electrodes may be configured to measure a bio impedance value of patient 4. In some examples, the plurality of electrodes of IMD 10 are configured to detect a signal indicative of an electric potential of the tissue surrounding the IMD 10. Moreover, IMD 10 may additionally or alternatively include one or more optical sensors, accelerometers, temperature sensors, chemical sensors, light sensors, pressure sensors, in some examples. Such sensors may detect one or more physiological parameters indicative of a patient condition.

External device 12 may be a hand-held computing device with a display viewable by the user and an interface for providing input to external device 12 (i.e., a user input mechanism). For example, external device 12 may include a small display screen (e.g., a liquid crystal display (LCD) or a light emitting diode (LED) display) that presents information to the user. In addition, external device 12 may include a touch screen display, keypad, buttons, a peripheral pointing device, voice activation, or another input mechanism that allows the user to navigate through the user interface of external device 12 and provide input. If external device 12 includes buttons and a keypad, the buttons may be dedicated to performing a certain function, e.g., a power button, the buttons and the keypad may be soft keys that change in function depending upon the section of the user interface currently viewed by the user, or any combination thereof.

In other examples, external device 12 may be a larger workstation or a separate application within another multi-function device, rather than a dedicated computing device. For example, the multi-function device may be a notebook computer, tablet computer, workstation, one or more servers, cellular phone, personal digital assistant, or another computing device that may run an application that enables the computing device to operate as a secure device.

When external device 12 is configured for use by the clinician, external device 12 may be used to transmit instructions to IMD 10 and to receive measurements, such as sensed bio impedance values. Example instructions may include requests to set electrode combinations for sensing and any other information that may be useful for programming into IMD 10. The clinician may also configure and store operational parameters for IMD 10 within IMD 10 with the aid of external device 12. In some examples, external device 12 assists the clinician in the configuration of IMD 10 by providing a system for identifying potentially beneficial operational parameter values.

Whether external device 12 is configured for clinician or patient use, external device 12 is configured to communicate with IMD 10 and, optionally, another computing device (not illustrated in FIG. 1), via wireless communication. External device 12, for example, may communicate via near-field communication technologies (e.g., inductive coupling, NFC or other communication technologies operable at ranges less than 10-20 cm) and far-field communication technologies (e.g., RF telemetry according to the 802.11 or Bluetooth® specification sets, or other communication technologies operable at ranges greater than near-field communication technologies).

Processing circuitry 14, in some examples, may include one or more processors that are configured to implement functionality and/or process instructions for execution within IMD 10. For example, processing circuitry 14 may be capable of processing instructions stored in a storage device. Processing circuitry 14 may include, for example, microprocessors, digital signal processors (DSPs), application specific integrated circuits (ASICs), field-programmable gate arrays (FPGAs), or equivalent discrete or integrated logic circuitry, or a combination of any of the foregoing devices or circuitry. Accordingly, processing circuitry 14 may include any suitable structure, whether in hardware, software, firmware, or any combination thereof, to perform the functions ascribed herein to processing circuitry 14.

Processing circuitry 14 may represent processing circuitry located within any combination of IMD 10 and external device 12. In some examples, processing circuitry 14 may be entirely located within a housing of IMD 10. In other examples, processing circuitry 14 may be entirely located within a housing of external device 12. In other examples, processing circuitry 14 may be located within any combination of IMD 10, external device 12, and another device or group of devices that are not illustrated in FIG. 1. As such, techniques and capabilities attributed herein to processing circuitry 14 may be attributed to any combination of IMD 10, external device 12, and other devices that are not illustrated in FIG. 1.

Medical device system 2 of FIG. 1 is an example of a system for measuring a bio impedance value according to one or more techniques of this disclosure. In some examples, processing circuitry 14 may include EGM analysis circuitry configured to determine one or more parameters of an EGM signal of patient 4. In one example, an EGM signal is sensed via a plurality of electrodes of IMD 10. An EGM is a signal representative of electrical activity of the heart, measured by electrodes implanted within the body, and often within the heart itself. For example, a cardiac EGM may include P-waves (depolarization of the atria), R-waves (depolarization of the ventricles), and T-waves (repolarization of the ventricles), among other events. Information relating to the aforementioned events, such as time separating one or more of the events, may be applied for a number of purposes, such as to determine whether an arrhythmia is occurring and/or predict whether an arrhythmia is likely to occur. Cardiac signal analysis circuitry, which may be implemented as part of processing circuitry 14, may perform signal processing techniques to extract information indicating the one or more parameters of the cardiac signal.

In some examples, IMD 10 includes one or more accelerometers. An accelerometer of IMD 10 may collect an accelerometer signal which reflects a measurement of a motion of patient 4. In some cases, the accelerometer may collect a three-axis accelerometer signal indicative of patient 4's movements within a three-dimensional Cartesian space. For example, the accelerometer signal may include a vertical axis accelerometer signal vector, a lateral axis accelerometer signal vector, and a frontal axis accelerometer signal vector. The vertical axis accelerometer signal vector may represent an acceleration of patient 4 along a vertical axis, the lateral axis accelerometer signal vector may represent an acceleration of patient 4 along a lateral axis, and the frontal axis accelerometer signal vector may represent an acceleration of patient 4 along a frontal axis. In some cases, the vertical axis substantially extends along a torso of patient 4 when patient 4 from a neck of patient 4 to a waist of patient 4, the lateral axis extends across a chest of patient 4 perpendicular to the vertical axis, and the frontal axis extends outward from and through the chest of patient 4, the frontal axis being perpendicular to the vertical axis and the lateral axis.

In some examples, processing circuitry 14 may be configured to identify, based on an accelerometer signal, that IMD 10 has flipped (e.g., turned so as to face another direction) from a previous position. For example, the plurality of electrodes of IMD 10 may not be anchored to surrounding tissue and IMD 10 may migrate in the body of patient 4. In some cases, IMD 10 may flip. Processing circuitry 14 may analyze accelerometer signals and determine that IMD 10 has flipped by determining that an accelerometer data in an accelerometer signal has reversed on one axis. In some examples, processing circuitry 14 may determine whether the measured bio impedance value is within a predetermined portion of the bio impedance measurement range based on determining that IMD 10 has flipped. In some examples, processing circuitry 14 may continuously monitor the accelerometer signals. In other examples, processing circuitry 14 may periodically monitor the accelerometer signals.

Although in one example IMD 10 takes the form of an ICM, in other examples, IMD 10 takes the form of any combination of implantable cardioverter defibrillators (ICDs) with intravascular or extravascular leads, pacemakers, cardiac resynchronization therapy devices (CRT-Ds), neuromodulation devices, left ventricular assist devices (LVADs), implantable sensors, orthopedic devices, or drug pumps, as examples. The bio impedance value of patient 4 may be measured using one or more of the aforementioned devices.

Figure 2:
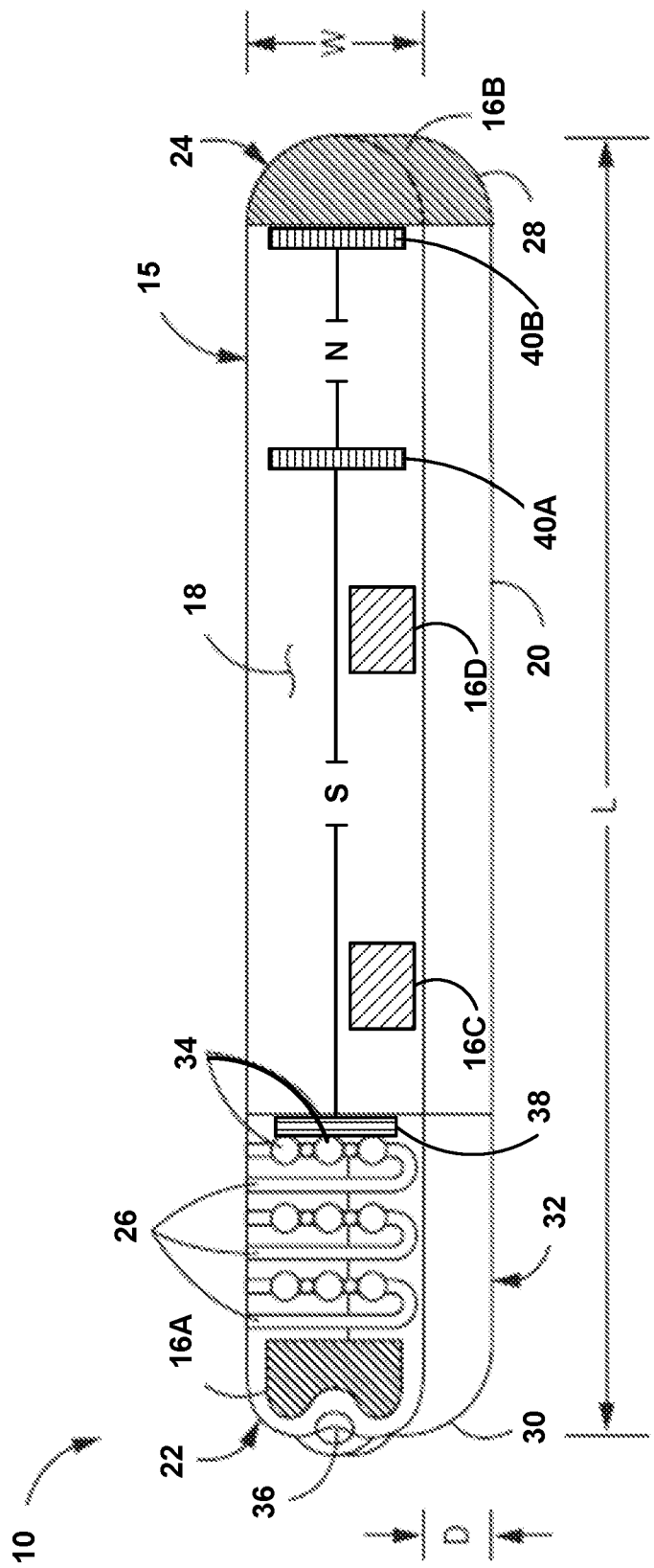
FIG. 2 is a conceptual drawing illustrating an example configuration of the implantable medical device (IMD) of the medical device system of FIG. 1, in accordance with one or more techniques described herein.

FIG. 2 is a conceptual drawing illustrating an example configuration of IMD 10 of the medical device system 2 of FIG. 1, in accordance with one or more techniques described herein. In the example shown in FIG. 2, IMD 10 may include a leadless, subcutaneously-implantable monitoring device having housing 15, proximal electrode 16A, and distal electrode 16B. Housing 15 may further include first major surface 18, second major surface 20, proximal end 22, and distal end 24. In some examples, IMD 10 may include one or more additional electrodes 16C, 16D positioned on one or both of major surfaces 18, 20 of IMD 10. Housing 15 encloses electronic circuitry located inside the IMD 10, and protects the circuitry contained therein from fluids such as body fluids. In some examples, electrical feedthroughs provide electrical connection of electrodes 16A-16D, and antenna 26, to circuitry within housing 15. In some examples, electrode 16B may be formed from an uninsulated portion of conductive housing 15.

In the example shown in FIG. 2, IMD 10 is defined by a length L, a width W, and thickness or depth D. In this example, IMD 10 is in the form of an elongated rectangular prism in which length L is significantly greater than width W, and in which width W is greater than depth D. However, other configurations of IMD 10 are contemplated, such as those in which the relative proportions of length L, width W, and depth D vary from those described and shown in FIG. 2. In some examples, the geometry of the IMD 10, such as the width W being greater than the depth D, may be selected to allow IMD 10 to be inserted under the skin of the patient using a minimally invasive procedure and to remain in the desired orientation during insertion. In addition, IMD 10 may include radial asymmetries (e.g., the rectangular shape) along a longitudinal axis of IMD 10, which may help maintain the device in a desired orientation following implantation.

In some examples, a spacing between proximal electrode 16A and distal electrode 16B may range from about 30-55 mm, about 35-55 mm, or about 40-55 mm, or more generally from about 25-60 mm. Overall, IMD 10 may have a length L of about 20-30 mm, about 40-60 mm, or about 45-60 mm. In some examples, the width W of major surface 18 may range from about 3-10 mm, and may be any single width or range of widths between about 3-10 mm. In some examples, a depth D of IMD 10 may range from about 2-9 mm. In other examples, the depth D of IMD 10 may range from about 2-5 mm, and may be any single or range of depths from about 2-9 mm. In any such examples, IMD 10 is sufficiently compact to be implanted within the subcutaneous space of patient 4 in the region of a pectoral muscle.

IMD 10, according to an example of the present disclosure, may have a geometry and size designed for ease of implant and patient comfort. Examples of IMD 10 described in this disclosure may have a volume of 3 cubic centimeters ($cm^3$) or less, 1.5 $cm^3$ or less, or any volume therebetween. In addition, in the example shown in FIG. 2, proximal end 22 and distal end 24 are rounded to reduce discomfort and irritation to surrounding tissue once implanted under the skin of patient 4.

In the example shown in FIG. 2, first major surface 18 of IMD 10 faces outward towards the skin, when IMD 10 is inserted within patient 4, whereas second major surface 20 is faces inward toward musculature of patient 4. Thus, first and second major surfaces 18, 20 may face in directions along a sagittal axis of patient 4 (see FIG. 1), and this orientation may be generally maintained upon implantation due to the dimensions of IMD 10.

Proximal electrode 16A and distal electrode 16B may be used to sense cardiac EGM signals (e.g., ECG signals) when IMD 10 is implanted subcutaneously in patient 4. In some examples, processing circuitry of IMD 10 also may determine whether cardiac ECG signals of patient 4 are indicative of arrhythmia or other abnormalities, which processing circuitry of IMD 10 may evaluate in determining whether a medical condition (e.g., heart failure, sleep apnea, or COPD) of patient 4 has changed. The cardiac ECG signals may be stored in a memory of IMD 10, and data derived from the cardiac ECG signals may be transmitted via integrated antenna 26 to another device, such as external device 12. In some examples, one or both of electrodes 16A and 16B also may be used by IMD 10 to sense bio impedance values during bio impedance measurements performed by IMD 10. In some examples, such sensed bio impedance values may be stored in the memory of IMD 10 and may be transmitted via integrated antenna 26 to another device, such as external device 12. In some examples, the sensed bio impedance values may be transmitted to another device on a periodic basis, such as daily. The sensed bio impedance values detected by IMD 10 may reflect a resistance value associated with a contact between electrodes 16A, 16B, and target tissue of patient 4. Additionally, in some examples, electrodes 16A, 16B may be used by communication circuitry of IMD 10 for tissue conductance communication (TCC) communication with external device 12 or another device.

In the example shown in FIG. 2, proximal electrode 16A is in close proximity to proximal end 22, and distal electrode 16B is in close proximity to distal end 24 of IMD 10. In this example, distal electrode 16B is not limited to a flattened, outward facing surface, but may extend from first major surface 18, around rounded edges 28 or end surface 30, and onto the second major surface 20 in a three-dimensional curved configuration. As illustrated, proximal electrode 16A is located on first major surface 18 and is substantially flat and outward facing. However, in other examples not shown here, proximal electrode 16A and distal electrode 16B both may be configured like proximal electrode 16A shown in FIG. 2, or both may be configured like distal electrode 16B shown in FIG. 2. In some examples, additional electrodes 16C and 16D may be positioned on one or both of first major surface 18 and second major surface 20, such that a total of four electrodes are included on IMD 10. Any of electrodes 16A-16D may be formed of a biocompatible conductive material. For example, any of electrodes 16A-16D may be formed from any of stainless steel, titanium, platinum, iridium, or alloys thereof. In addition, electrodes of IMD 10 may be coated with a material such as titanium nitride or fractal titanium nitride, although other suitable materials and coatings for such electrodes may be used.

In the example shown in FIG. 2, proximal end 22 of IMD 10 includes header assembly 32 having one or more of proximal electrode 16A, integrated antenna 26, anti-migration projections 34, and suture hole 36. Integrated antenna 26 is located on the same major surface (e.g., first major surface 18) as proximal electrode 16A, and may be an integral part of header assembly 32. In other examples, integrated antenna 26 may be formed on the major surface opposite from proximal electrode 16A, or, in still other examples, may be incorporated within housing 15 of IMD 10. Antenna 26 may be configured to transmit or receive electromagnetic signals for communication. For example, antenna 26 may be configured to transmit to or receive signals from a programmer via inductive coupling, electromagnetic coupling, tissue conductance, Near Field Communication (NFC), Radio Frequency Identification (RFID), Bluetooth®, WiFi®, or other proprietary or non-proprietary wireless telemetry communication schemes. Antenna 26 may be coupled to communication circuitry of IMD 10, which may drive antenna 26 to transmit signals to external device 12, and may transmit signals received from external device 12 to processing circuitry of IMD 10 via communication circuitry.

In some examples, IMD 10 may include several features for retaining IMD 10 in position once subcutaneously implanted in patient 4, so as to decrease the chance that IMD 10 migrates in the body of patient 4. For example, as shown in FIG. 2, housing 15 may include anti-migration projections 34 positioned adjacent integrated antenna 26. Anti-migration projections 34 may include a plurality of bumps or protrusions extending away from first major surface 18, and may help prevent longitudinal movement of IMD 10 after implantation in patient 4. In other examples, anti-migration projections 34 may be located on the opposite major surface as proximal electrode 16A and/or integrated antenna 26. In addition, in the example shown in FIG. 2 header assembly 32 includes suture hole 36, which provides another means of securing IMD 10 to the patient to prevent movement following insertion. In the example shown, suture hole 36 is located adjacent to proximal electrode 16A. In some examples, header assembly 32 may include a molded header assembly made from a polymeric or plastic material, which may be integrated or separable from the main portion of IMD 10.

Electrodes 16A and 16B may be used to sense cardiac ECG signals, as described above. Additional electrodes 16C and 16D may be used to sense subcutaneous tissue bio impedance, in addition to or instead of electrodes 16A, 16B, in some examples. In some examples, processing circuitry of IMD 10 may determine a bio impedance value of patient 4 based on signals received from at least two of electrodes 16A-16D. For example, processing circuitry of IMD 10 may generate an excitation signal, such as a current or voltage signal, deliver the signal via a selected two or more of electrodes 16A-16D, and measure the resulting other of current or voltage. Processing circuitry of IMD 10 may determine a bio impedance value based on the delivered excitation signal and the measured voltage or current.

In the example shown in FIG. 2, IMD 10 includes a light emitter 38, a proximal light detector 40A, and a distal light detector 40B positioned on housing 15 of IMD 10. Light detector 40A may be positioned at a distance S from light emitter 38, and a distal light detector 40B positioned at a distance S+N from light emitter 38. In other examples, IMD 10 may include only one of light detectors 40A, 40B, or may include additional light emitters and/or additional light detectors. Although light emitter 38 and light detectors 40A, 40B are described herein as being positioned on housing 15 of IMD 10, in other examples, one or more of light emitter 38 and light detectors 40A, 40B may be positioned, on a housing of another type of IMD within patient 4, such as a transvenous, subcutaneous, or extravascular pacemaker or ICD, or connected to such a device via a lead.

As shown in FIG. 2, light emitter 38 may be positioned on header assembly 32, although, in other examples, one or both of light detectors 40A, 40B may additionally or alternatively be positioned on header assembly 32. In some examples, light emitter 38 may be positioned on a medial section of IMD 10, such as part way between proximal end 22 and distal end 24. Although light emitter 38 and light detectors 40A, 40B are illustrated as being positioned on first major surface 18, light emitter 38 and light detectors 40A, 40B alternatively may be positioned on second major surface 20. In some examples, IMD may be implanted such that light emitter 38 and light detectors 40A, 40B face inward when IMD 10 is implanted, toward the muscle of patient 4, which may help minimize interference from background light coming from outside the body of patient 4. Light detectors 40A, 40B may include a glass or sapphire window, such as described below with respect to FIG. 4B, or may be positioned beneath a portion of housing 15 of IMD 10 that is made of glass or sapphire, or otherwise transparent or translucent.

In some examples, IMD 10 may include one or more additional sensors, such as one or more accelerometers (not shown in FIG. 2). Such accelerometers may be 3D accelerometers configured to generate signals indicative of one or more types of movement of the patient, such as gross body movement (e.g., motion) of the patient, patient posture, movements associated with the beating of the heart, or coughing, rales, or other respiration abnormalities, or the movement of IMD 10 within the body of patient 4. One or more of the parameters monitored by IMD 10 (e.g., bio impedance, EGM) may fluctuate in response to changes in one or more such types of movement. For example, changes in parameter values sometimes may be attributable to increased patient motion (e.g., exercise or other physical motion as compared to immobility) or to changes in patient posture, and not necessarily to changes in a medical condition. Thus, in some methods of identifying or tracking a medical condition of patient 4, it may be advantageous to account for such fluctuations when determining whether a change in a parameter is indicative of a change in a medical condition. Additionally, data within an accelerometer signal reversing may be indicative of IMD 10 flipping. It may be advantageous to determine whether a measured bio impedance value is within a predetermined portion of a bio impedance measurement range based on determining that IMD 10 has migrated or flipped in the body of patient 4, as the tissue electrodes 16A-16D may be in contact with may change when IMD 10 migrates or flips.

Figure 3:
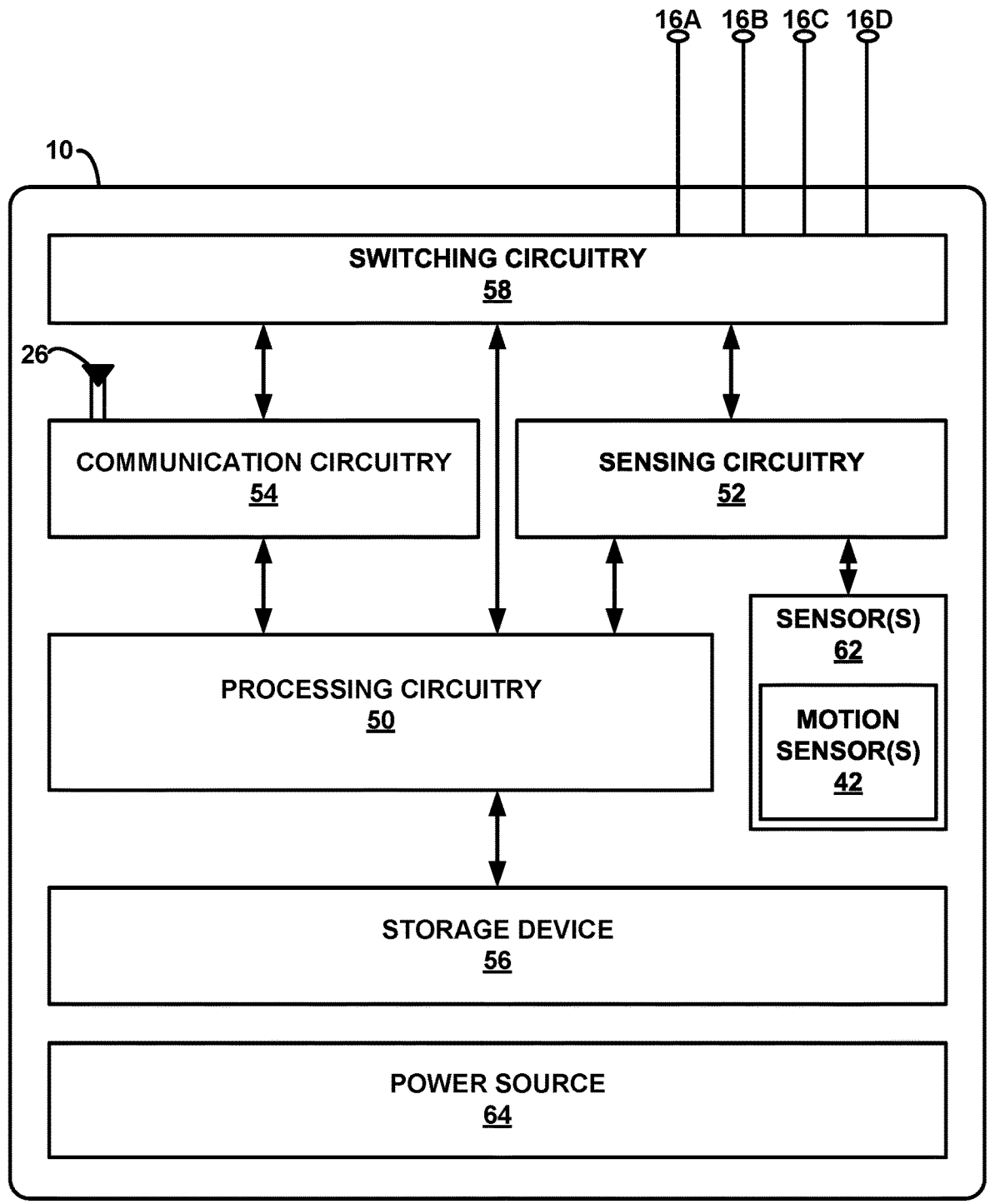
FIG. 3 is a functional block diagram illustrating an example configuration of the IMD of FIGS. 1 and 2, in accordance with one or more techniques described herein.

FIG. 3 is a functional block diagram illustrating an example configuration of IMD 10 of FIGS. 1 and 2, in accordance with one or more techniques described herein. In the illustrated example, IMD 10 includes electrodes 16, antenna 26, processing circuitry 50, sensing circuitry 52, communication circuitry 54, storage device 56, switching circuitry 58, sensors 62 including motion sensor(s) 42 (which may be an accelerometer), and power source 64. Although not illustrated in FIG. 3, sensors 62 may include light detectors 40 of FIG. 2.

Processing circuitry 50 may include fixed function circuitry and/or programmable processing circuitry. Processing circuitry 50 may include any one or more of a microprocessor, a controller, a DSP, an ASIC, an FPGA, or equivalent discrete or analog logic circuitry. In some examples, processing circuitry 50 may include multiple components, such as any combination of one or more microprocessors, one or more controllers, one or more DSPs, one or more ASICs, or one or more FPGAs, as well as other discrete or integrated logic circuitry. The functions attributed to processing circuitry 50 herein may be embodied as software, firmware, hardware or any combination thereof. In some examples, one or more techniques of this disclosure may be performed by processing circuitry 50.

Sensing circuitry 52 and communication circuitry 54 may be selectively coupled to electrodes 16A-16D via switching circuitry 58, as controlled by processing circuitry 50. Sensing circuitry 52 may monitor signals from electrodes 16A-16D in order to monitor electrical activity of heart (e.g., to produce an ECG), and/or bio impedance, the bio impedance being indicative of at least some aspects of patient 4's fluid retention and respiratory patterns. Sensing circuitry 52 also may monitor signals from sensors 62, which may include motion sensor(s) 42 (which may be an accelerometer), and any additional light detectors that may be positioned on IMD 10. In some examples, sensing circuitry 52 may include one or more filters and amplifiers for filtering and amplifying signals received from one or more of electrodes 16A-16D and/or motion sensor(s) 42 (which may be an accelerometer).

Communication circuitry 54 may include any suitable hardware, firmware, software or any combination thereof for communicating with another device, such as external device 12 or another IMD or sensor, such as a pressure sensing device. Under the control of processing circuitry 50, communication circuitry 54 may receive downlink telemetry from, as well as send uplink telemetry to, external device 12 or another device with the aid of an internal or external antenna, e.g., antenna 26. In addition, processing circuitry 50 may communicate with a networked computing device via an external device (e.g., external device 12) and a computer network, such as the Medtronic CareLink® Network developed by Medtronic, plc, of Dublin, Ireland.

A clinician or other user may retrieve data from IMD 10 using external device 12, or by using another local or networked computing device configured to communicate with processing circuitry 50 via communication circuitry 54. The clinician may also program parameters of IMD 10 using external device 12 or another local or networked computing device.

In some examples, storage device 56 includes computer-readable instructions that, when executed by processing circuitry 50, cause IMD 10 and processing circuitry 50 to perform various functions attributed to IMD 10 and processing circuitry 50 herein. Storage device 56 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Power source 64 is configured to deliver operating power to the components of IMD 10. Power source 64 may include a battery and a power generation circuit to produce the operating power. In some examples, the battery is rechargeable to allow extended operation. In some examples, recharging is accomplished through proximal inductive interaction between an external charger and an inductive charging coil within external device 12. Power source 64 may include any one or more of a plurality of different battery types, such as nickel cadmium batteries and lithium ion batteries. A non-rechargeable battery may be selected to last for several years, while a rechargeable battery may be inductively charged from an external device, e.g., on a daily or weekly basis.

Figure 4A:
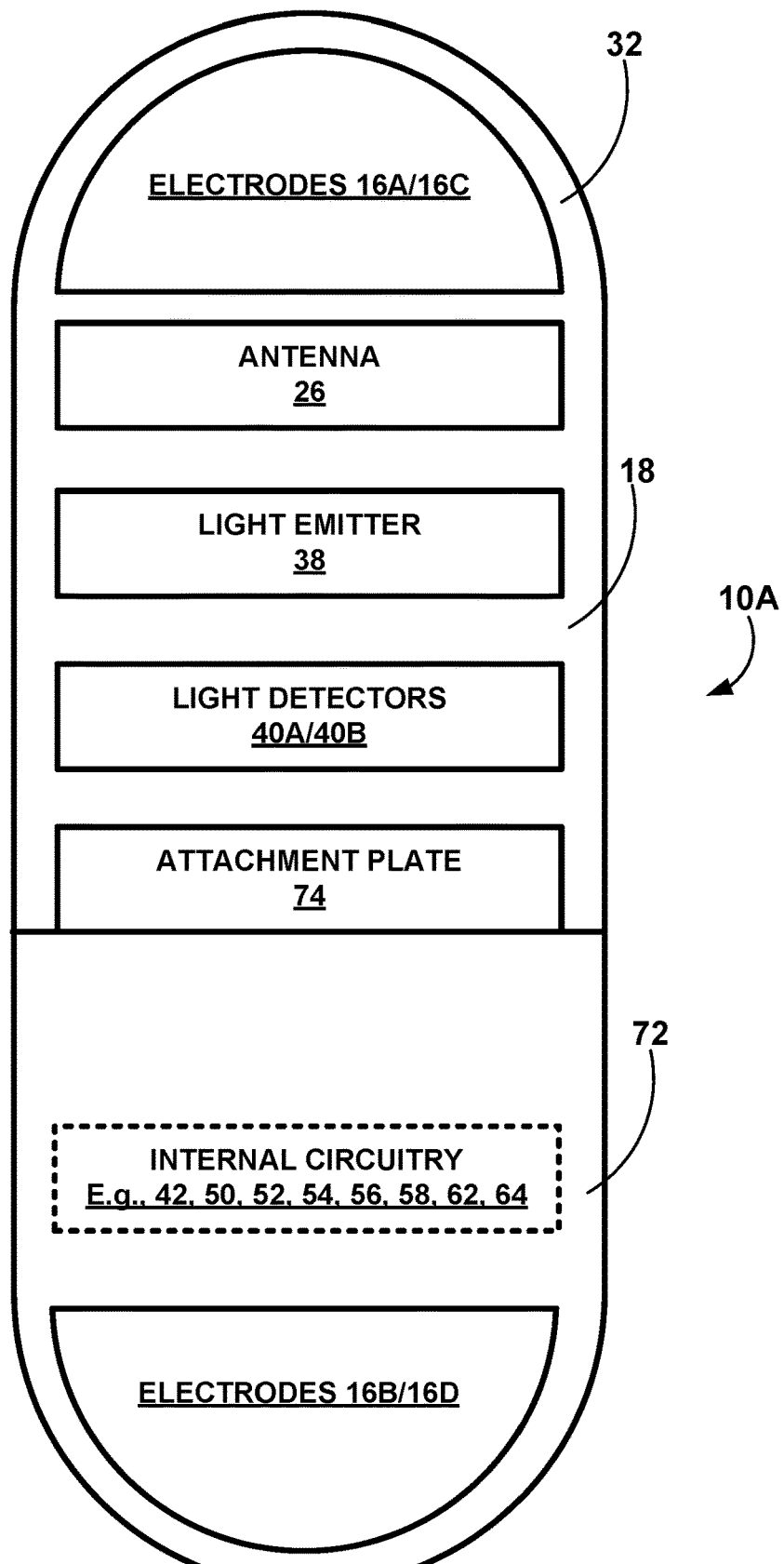
FIGS. 4A and 4B are block diagrams illustrating two additional example IMDs that may be substantially similar to the IMD of FIGS. 1-3, but which may include one or more additional features, in accordance with one or more techniques described herein.
Figure 4B:
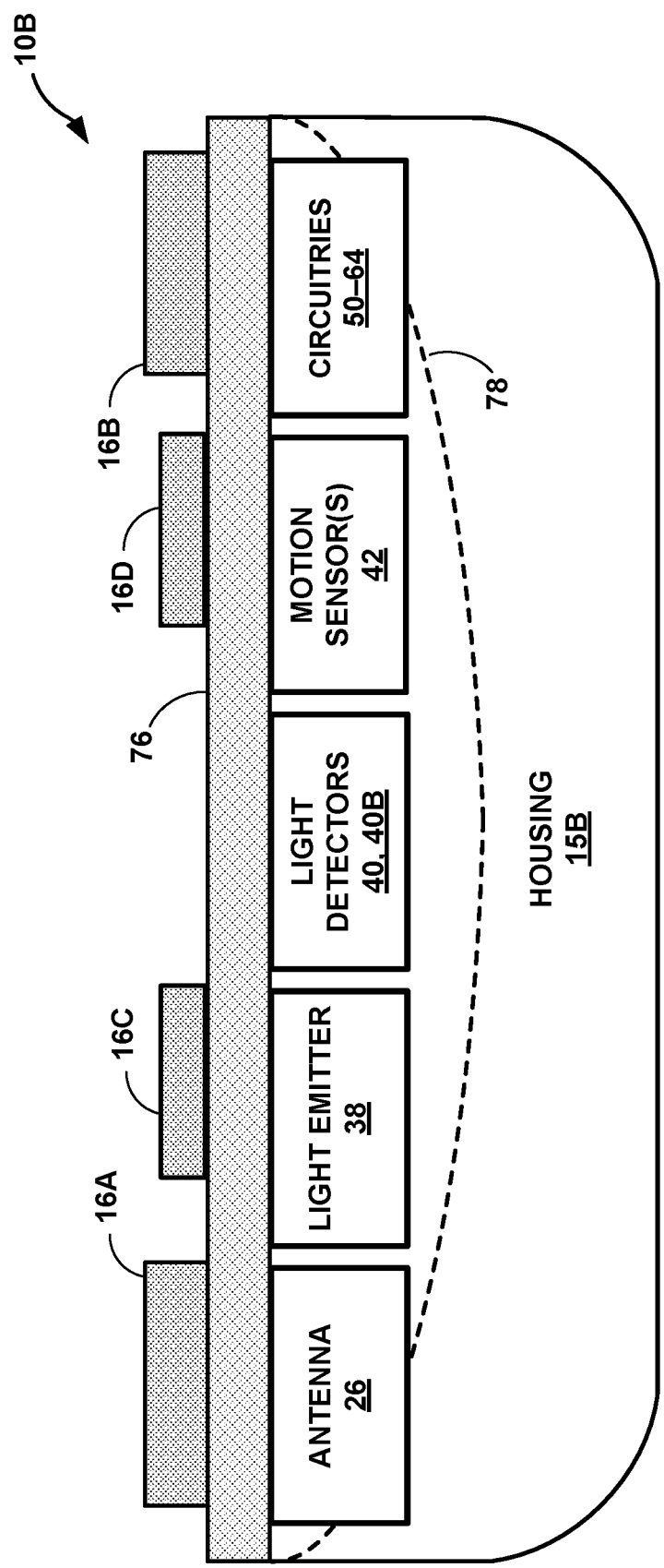

FIGS. 4A and 4B illustrate two additional example IMDs that may be substantially similar to IMD 10 of FIGS. 1-3, but which may include one or more additional features, in accordance with one or more techniques described herein. The components of FIGS. 4A and 4B may not necessarily be drawn to scale, but instead may be enlarged to show detail. FIG. 4A is a block diagram of a top view of an example configuration of an IMD 10A. FIG. 4B is a block diagram of a side view of example IMD 10B, which may include an insulative layer as described below.

FIG. 4A is a conceptual drawing illustrating another example IMD 10A that may be substantially similar to IMD 10 of FIG. 1. In addition to the components illustrated in FIGS. 1-3, the example of IMD 10 illustrated in FIG. 4A also may include a body portion 72 and an attachment plate 74. Attachment plate 74 may be configured to mechanically couple header assembly 32 to body portion 72 of IMD 10A. Body portion 72 of IMD 10A may be configured to house one or more of the internal components of IMD 10 illustrated in FIG. 3, such as one or more of processing circuitry 50, sensing circuitry 52, communication circuitry 54, storage device 56, switching circuitry 58, internal components of sensors 62, and power source 64. In some examples, body portion 72 may be formed of one or more of titanium, ceramic, or any other suitable biocompatible materials.

FIG. 4B is a conceptual drawing illustrating another example IMD 10B that may include components substantially similar to IMD 10 of FIG. 1. In addition to the components illustrated in FIGS. 1-3, the example of IMD 10B illustrated in FIG. 4B also may include a wafer-scale insulative cover 76, which may help insulate electrical signals passing between electrodes 16A-16D and/or light detectors 40A, 40B on housing 15B and processing circuitry 50. In some examples, insulative cover 76 may be positioned over an open housing 15 to form the housing for the components of IMD 10B. One or more components of IMD 10B (e.g., antenna 26, light emitter 38, light detectors 40A, 40B, processing circuitry 50, sensing circuitry 52, communication circuitry 54, switching circuitry 58, and/or power source 64) may be formed on a bottom side of insulative cover 76, such as by using flip-chip technology. Insulative cover 76 may be flipped onto a housing 15B. When flipped and placed onto housing 15B, the components of IMD 10B formed on the bottom side of insulative cover 76 may be positioned in a gap 78 defined by housing 15B.

Insulative cover 76 may be configured so as not to interfere with the operation of IMD 10B. For example, one or more of electrodes 16A-16D may be formed or placed above or on top of insulative cover 76, and electrically connected to switching circuitry 58 through one or more vias (not shown) formed through insulative cover 76. Insulative cover 76 may be formed of sapphire (i.e., corundum), glass, parylene, and/or any other suitable insulating material. Sapphire may be greater than 80% transmissive for wavelengths in the range of about 300 nm to about 4000 nm, and may have a relatively flat profile. In the case of variation, different transmissions at different wavelengths may be compensated for, such as by using a ratiometric approach. In some examples, insulative cover 76 may have a thickness of about 300 micrometers to about 600 micrometers. Housing 15B may be formed from titanium or any other suitable material (e.g., a biocompatible material), and may have a thickness of about 200 micrometers to about 500 micrometers. These materials and dimensions are examples only, and other materials and other thicknesses are possible for devices of this disclosure.

Figure 5:
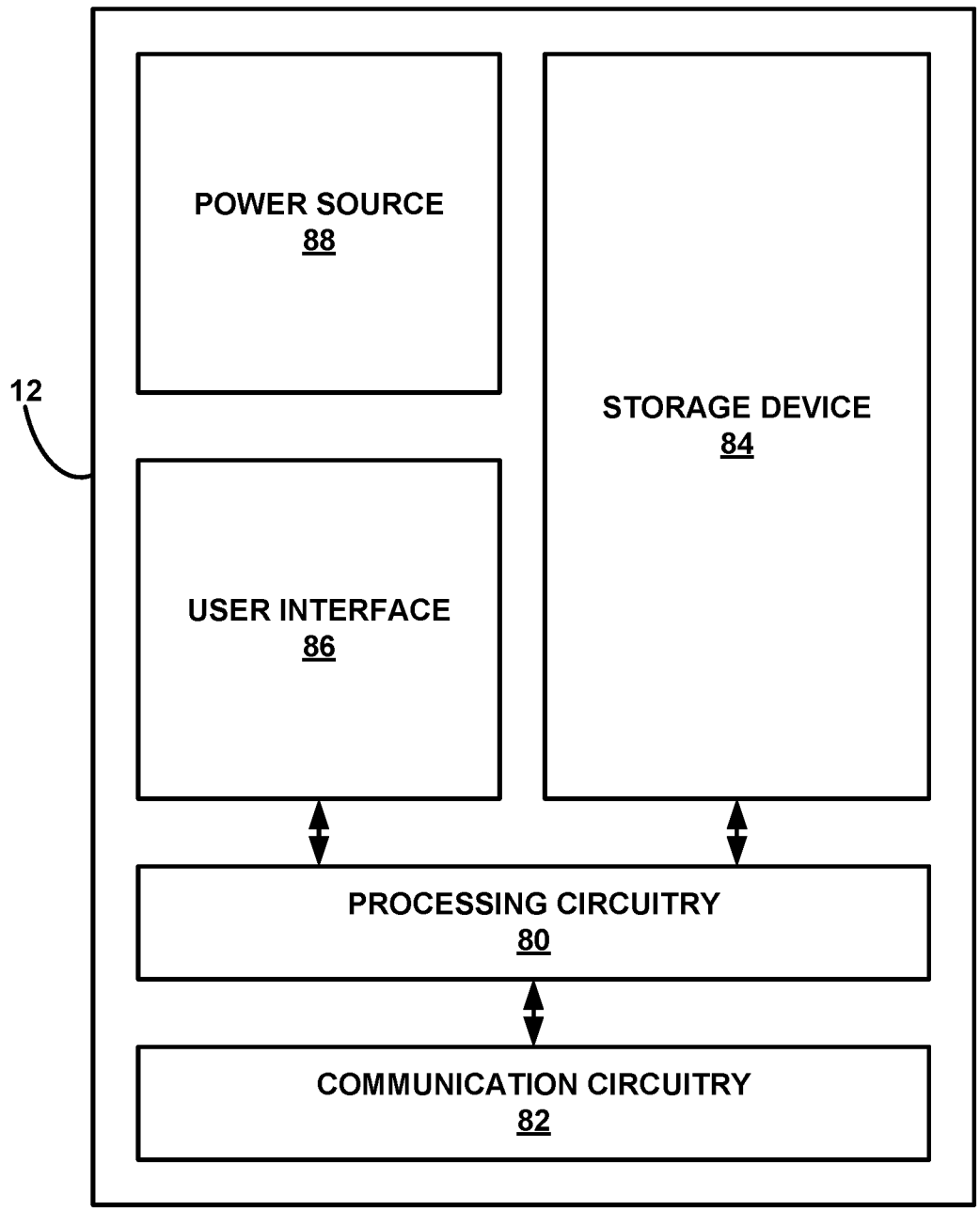
FIG. 5 is a block diagram illustrating an example configuration of components of the external device of FIG. 1, in accordance with one or more techniques of this disclosure.

FIG. 5 is a block diagram illustrating an example configuration of components of external device 12, in accordance with one or more techniques of this disclosure. In the example of FIG. 5, external device 12 includes processing circuitry 80, communication circuitry 82, storage device 84, user interface 86, and power source 88.

Processing circuitry 80, in one example, may include one or more processors that are configured to implement functionality and/or process instructions for execution within external device 12. For example, processing circuitry 80 may be capable of processing instructions stored in storage device 84. Processing circuitry 80 may include, for example, microprocessors, DSPs, ASICs, FPGAs, or equivalent discrete or integrated logic circuitry, or a combination of any of the foregoing devices or circuitry. Accordingly, processing circuitry 80 may include any suitable structure, whether in hardware, software, firmware, or any combination thereof, to perform the functions ascribed herein to processing circuitry 80. In some examples, processing circuitry 80 may perform one or more of the techniques of this disclosure.

Communication circuitry 82 may include any suitable hardware, firmware, software or any combination thereof for communicating with another device, such as IMD 10. Under the control of processing circuitry 80, communication circuitry 82 may receive downlink telemetry from, as well as send uplink telemetry to, IMD 10, or another device.

Storage device 84 may be configured to store information within external device 12 during operation. Storage device 84 may include a computer-readable storage medium or computer-readable storage device. In some examples, storage device 84 includes one or more of a short-term memory or a long-term memory. Storage device 84 may include, for example, RAM, dynamic random access memories (DRAM), static random access memories (SRAM), magnetic discs, optical discs, flash memories, or forms of electrically programmable memories (EPROM) or EEPROM. In some examples, storage device 84 is used to store data indicative of instructions for execution by processing circuitry 80. Storage device 84 may be used by software or applications running on external device 12 to temporarily store information during program execution.

Data exchanged between external device 12 and IMD 10 may include operational parameters. External device 12 may transmit data including computer readable instructions which, when implemented by IMD 10, may control IMD 10 to change one or more operational parameters and/or export collected data. For example, processing circuitry 80 may transmit an instruction to IMD 10 which requests IMD 10 to export collected data (e.g., data corresponding to one or more of an ECG signal, bio impedance value(s) or an accelerometer signal) to external device 12. In turn, external device 12 may receive the collected data from IMD 10 and store the collected data in storage device 84. Additionally, or alternatively, processing circuitry 80 may export instructions to IMD 10 requesting IMD 10 to update one or more operational parameters of IMD 10.

A user, such as a clinician or patient 4, may interact with external device 12 through user interface 86. User interface 86 includes a display (not shown), such as an LCD or LED display or other type of screen, with which processing circuitry 80 may present information related to IMD 10 (e.g., EGM signals obtained from at least one electrode or at least one electrode combination or bio impedance values). In addition, user interface 86 may include an input mechanism to receive input from the user. The input mechanisms may include, for example, any one or more of buttons, a keypad (e.g., an alphanumeric keypad), a peripheral pointing device, a touch screen, or another input mechanism that allows the user to navigate through user interfaces presented by processing circuitry 80 of external device 12 and provide input. In other examples, user interface 86 also includes audio circuitry for providing audible notifications, instructions or other sounds to patient 4, receiving voice commands from patient 4, or both. Storage device 84 may include instructions for operating user interface 86 and for managing power source 88.

Power source 88 is configured to deliver operating power to the components of external device 12. Power source 88 may include a battery and a power generation circuit to produce the operating power. In some examples, the battery is rechargeable to allow extended operation. Recharging may be accomplished by electrically coupling power source 88 to a cradle or plug that is connected to an alternating current (AC) outlet. In addition, recharging may be accomplished through proximal inductive interaction between an external charger and an inductive charging coil within external device 12. In other examples, traditional batteries (e.g., nickel cadmium or lithium ion batteries) may be used. In addition, external device 12 may be directly coupled to an alternating current outlet to operate.

Figure 6:
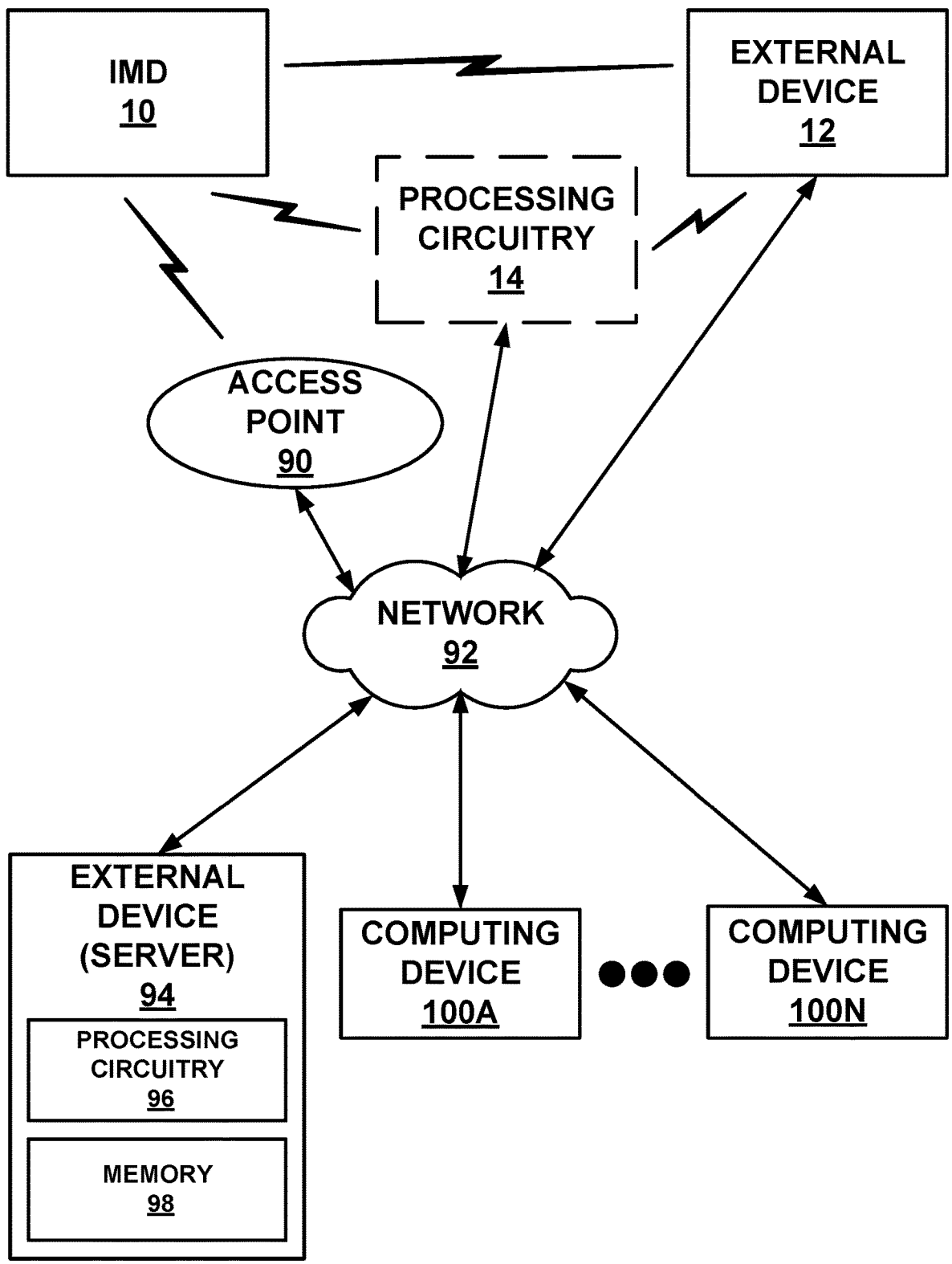
FIG. 6 is a block diagram illustrating an example system that includes an access point, a network, external computing devices, such as a server, and one or more other computing devices, which may be coupled to the IMD of FIGS. 1-4, an external device, and processing circuitry via a network, in accordance with one or more techniques described herein.

FIG. 6 is a block diagram illustrating an example system that includes an access point 90, a network 92, external computing devices, such as a server 94, and one or more other computing devices 100A-100N, which may be coupled to IMD 10, external device 12, and processing circuitry 14 via network 92, in accordance with one or more techniques described herein. In this example, IMD 10 may use communication circuitry 54 to communicate with external device 12 via a first wireless connection, and to communication with an access point 90 via a second wireless connection. In the example of FIG. 6, access point 90, external device 12, server 94, and computing devices 100A-100N are interconnected and may communicate with each other through network 92.

Access point 90 may include a device that connects to network 92 via any of a variety of connections, such as telephone dial-up, digital subscriber line (DSL), or cable modem connections. In other examples, access point 90 may be coupled to network 92 through different forms of connections, including wired or wireless connections. In some examples, access point 90 may be a user device, such as a tablet or smartphone, that may be co-located with the patient. As discussed above, IMD 10 may be configured to transmit data, such as any one or combination of an EGM signal, bio impedance values, or an accelerometer signal to external device 12. In addition, access point 90 may interrogate IMD 10, such as periodically or in response to a command from the patient or network 92, in order to retrieve parameter values determined by processing circuitry 50 of IMD 10, or other operational or patient data from IMD 10. Access point 90 may then communicate the retrieved data to server 94 via network 92.

In some cases, server 94 may be configured to provide a secure storage site for data that has been collected from IMD 10, and/or external device 12, such as bio impedance values or heart failure scores. In some cases, server 94 may assemble data in web pages or other documents for viewing by trained professionals, such as clinicians, via computing devices 100A-100N. One or more aspects of the illustrated system of FIG. 6 may be implemented with general network technology and functionality, which may be similar to that provided by the Medtronic CareLink® Network developed by Medtronic plc, of Dublin, Ireland.

Server 94 may include processing circuitry 96. Processing circuitry 96 may include fixed function circuitry and/or programmable processing circuitry. Processing circuitry 96 may include any one or more of a microprocessor, a controller, a DSP, an ASIC, an FPGA, or equivalent discrete or analog logic circuitry. In some examples, processing circuitry 96 may include multiple components, such as any combination of one or more microprocessors, one or more controllers, one or more DSPs, one or more ASICs, or one or more FPGAs, as well as other discrete or integrated logic circuitry. The functions attributed to processing circuitry 96 herein may be embodied as software, firmware, hardware or any combination thereof. In some examples, processing circuitry 96 may perform one or more techniques described herein. In some examples, processing circuitry 96 may determine heart failure scores based on sensed bio impedance values by IMD 10.

Server 94 may include memory 98. Memory 98 includes computer-readable instructions that, when executed by processing circuitry 96, cause IMD 10 and processing circuitry 96 to perform various functions attributed to IMD 10 and processing circuitry 96 herein. Memory 98 may include any volatile, non-volatile, magnetic, optical, or electrical media, such as RAM, ROM, NVRAM, EEPROM, flash memory, or any other digital media.

In some examples, one or more of computing devices 100A-100N (e.g., device 100A) may be a tablet or other smart device located with a clinician, by which the clinician may program, receive alerts from, and/or interrogate IMD 10. For example, the clinician may access data corresponding to bio impedance values, an EGM signal and/or an accelerometer signal collected by IMD 10 through device 100A, such as when patient 4 is in between clinician visits, to check on a status of a medical condition, such as heart failure. In some examples, the clinician may enter instructions for a medical intervention for patient 4 into an app in device 100A, such as based on a status of a patient condition determined by IMD 10, external device 12, processing circuitry 14, or any combination thereof, or based on other patient data known to the clinician. Device 100A then may transmit the instructions for medical intervention to another of computing devices 100A-100N (e.g., device 100B) located with patient 4 or a caregiver of patient 4. For example, such instructions for medical intervention may include an instruction to change a drug dosage, timing, or selection, to schedule a visit with the clinician, or to seek medical attention. In further examples, device 100B may generate an alert to patient 4 based on a status of a medical condition of patient 4 determined by IMD 10, which may enable patient 4 proactively to seek medical attention prior to receiving instructions for a medical intervention. In this manner, patient 4 may be empowered to take action, as needed, to address his or her medical status, which may help improve clinical outcomes for patient 4.

Figure 7:
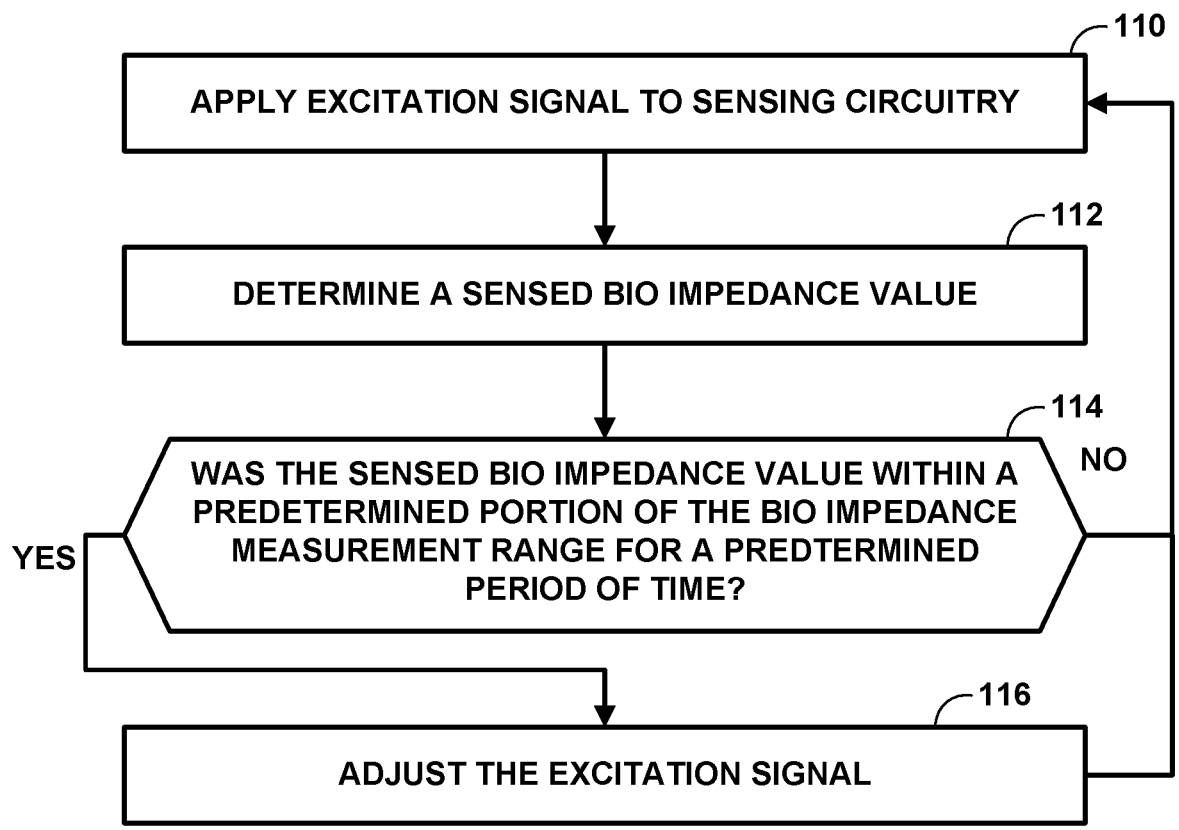
FIG. 7 is a flow diagram illustrating an example of dynamically adjusting a bio impedance measurement range in accordance with one or more techniques of this disclosure.

FIG. 7 is a flow diagram illustrating an example of dynamically adjusting an impedance measurement range in accordance with one or more techniques of this disclosure. The example of FIG. 7 is focused on processing circuitry 50 of IMD 10 performing one or more of the techniques of this disclosure. However, processing circuitry 14, processing circuitry 50, processing circuitry 80, processing circuitry 96, or any combination thereof, may perform one or more of the techniques of this disclosure.

Processing circuitry 50 may apply an excitation signal to sensing circuitry 52 (110). For example, processing circuitry 50 may apply an excitation current or voltage to sensing circuitry 52. The excitation signal may be associated with a bio impedance measurement range within which a bio impedance value of patient 4 may be sensed or measured. For example, the bio impedance measurement range may be from 1000 ohms to 3000 ohms. Processing circuitry 50 may determine a sensed bio impedance value (112). For example, sensing circuitry 52 may deliver the excitation signal (e.g., a current or voltage) via one or more of electrodes 16A-16D and processing circuitry 50 may measure the resulting other of current or voltage. Processing circuitry 50 may determine whether the sensed bio impedance value was within a predetermined portion of the bio impedance measurement range for a predetermined period of time (114). For example, processing circuitry 50 may determine whether the sensed bio impedance value was at the top or the bottom of the bio impedance measurement range for a number of days, such as two or three days. In some examples, the predetermined portion of the bio impedance measurement range may be a percentage of the range, such as the top 10% to 25% of the bio impedance measurement range or the bottom 10% to 25% of the bio impedance measurement range. In some examples, the predetermined portion of the bio impedance measurement range may be a number of ohms such as within 200 ohms of the upper boundary limit of the bio impedance measurement range or within 200 ohms of the lower boundary limit of the bio impedance measurement range. In some examples, processing circuitry 50 may determine whether the sensed bio impedance value was within a predetermined portion of the bio impedance measurement range for a predetermined period of time on a periodic basis, such as daily. In some examples, processing circuitry 50 is configured to may determine whether the sensed bio impedance value was within a predetermined portion of the bio impedance measurement range for a predetermined period of time automatically (e.g., without intervention from a clinician or patient).

If the sensed bio impedance value was within the predetermined portion of the bio impedance measurement range for the predetermined period of time (the "YES" path in FIG. 7), processing circuitry 50 may adjust the excitation signal (116). For example, by increasing an excitation current, the bio impedance measurement range may become smaller by a decrease in the upper boundary limit of the bio impedance measurement range. By decreasing an excitation current, the bio impedance measurement range may become larger by an increase in the upper boundary limit of the bio impedance measurement range. Processing circuitry 50 may apply the adjusted excitation signal to sensing circuitry 52 (110).

For example, processing circuitry 50 may change the current or the voltage to adjust the bio impedance measurement range. In some examples, processing circuitry 50 may determine the adjusted excitation signal based upon the sensed bio impedance value. For example, one may determine in a laboratory environment that for a given bio impedance value, the required excitation signal value to place the sensed bio impedance value in the center of an adjusted bio impedance measurement range. A look-up table may be stored in storage device 56 which may include a number of excitation signal values to be applied for different sensed bio impedance values to change the adjusted bio impedance measurement range so that the sensed bio impedance value may be at the center or toward the center of the adjusted bio impedance measurement range. Alternatively, a formula may be used by processing circuitry 50 to determine the adjusted excitation signal based on the sensed bio impedance value.

In some examples, processing circuitry 50 may adjust the bio impedance measurement range such that the measured bio impedance value is closer to the center of the adjusted bio impedance measurement range than it was in the bio impedance measurement range prior to the adjustment. In some examples, the measured bio impedance value may not be in a predetermined portion of the adjusted bio impedance measurement range that corresponds to the predetermined portion of the bio impedance measurement range prior to the adjustment. For example, the measured bio impedance value may not be in the top x % or the bottom y % or the top x ohms or the bottom y ohms of the adjusted bio impedance measurement range.

If the sensed bio impedance value was not within the predetermined portion of the bio impedance measurement range for a predetermined period of time (the "NO" path of FIG. 7), processing circuitry 50 may not adjust the excitation signal and may apply the same excitation signal to sensing circuitry 52 (110) the next time processing circuitry 50 attempts to determine a sensed bio impedance value.

Figure 8:
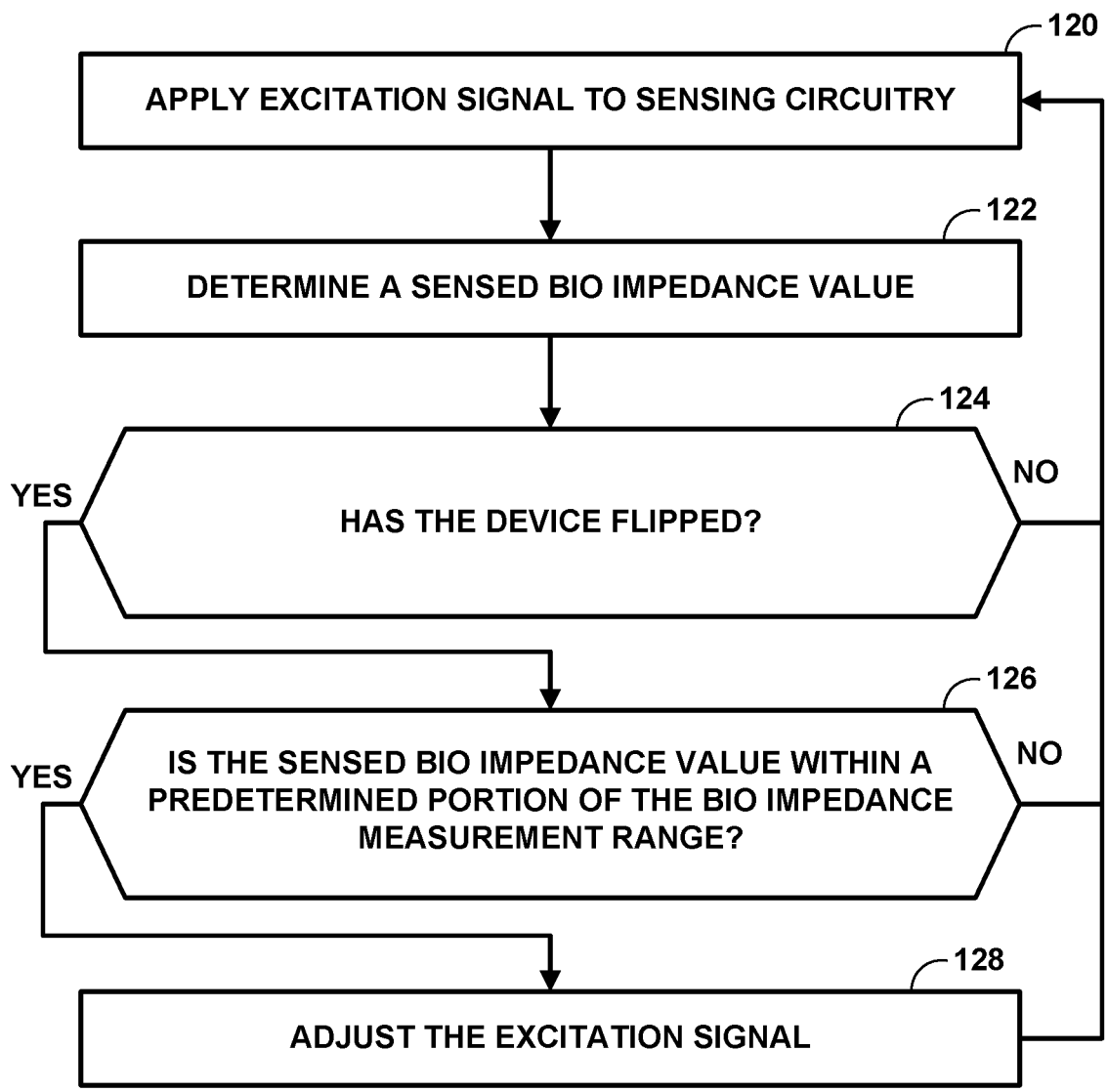
FIG. 8 is a flow diagram illustrating another example of dynamically adjusting a bio impedance measurement range in accordance with one or more techniques of this disclosure.

FIG. 8 is a flow diagram illustrating another example of dynamically adjusting an impedance measurement range in accordance with one or more techniques of this disclosure. The techniques of the example of FIG. 8 may be used together with the techniques of the example of FIG. 7 or may be used separately. The example of FIG. 8 is focused on processing circuitry 50 of IMD 10 performing one or more of the techniques of this disclosure. However, processing circuitry 14, processing circuitry 50, processing circuitry 80, processing circuitry 96, or any combination thereof, may perform one or more of the techniques of this disclosure.

Processing circuitry 50 may apply an excitation signal to sensing circuitry 52 (120). For example, processing circuitry 50 may apply an excitation current or voltage to sensing circuitry 52. The excitation signal may be associated with a bio impedance measurement range within which a bio impedance value of patient 4 may be measured. Processing circuitry 50 may determine a sensed bio impedance value (122). For example, sensing circuitry 52 may deliver the excitation signal (e.g., a current or voltage) via one or more of electrodes 16A-16D and processing circuitry 50 may measure the resulting other of current or voltage.

Processing circuitry 50 may determine whether IMD 10 has flipped (124). For example, processing circuitry 50 may monitor, continuously or periodically, a signal from an accelerometer to determine whether IMD 10 has flipped. A reversal of data in an accelerometer signal may be indicative of IMD 10 having flipped. In this case, electrodes 16A-16D may be contacting different tissue than before IMD 10 flipped which may cause the sensed bio impedance value to change. If IMD 10 has not flipped (the "NO" path from box 124), processing circuitry 50 may not adjust the excitation signal and may apply the same excitation signal to sensing circuitry 52 (110) the next time processing circuitry 50 attempts to determine a sensed bio impedance value.

If IMD 10 has flipped (the "YES" path from box 124), processing circuitry 50 may determine whether the sensed bio impedance value is within a predetermined portion of the bio impedance measurement range based on the determination that IMD 10 has flipped (126). For example, processing circuitry 50 may determine whether the sensed bio impedance value is at the top or the bottom of the bio impedance measurement range. In some examples, the predetermined portion of the bio impedance measurement range may be a percentage of the range or number of ohms, such as the top x % or the bottom y % or the top x ohms or the bottom y ohms. In some examples, x may equal y. In other examples, x may not equal y.

If the sensed bio impedance value is within the predetermined portion of the bio impedance measurement range (the "YES" path from box 126), processing circuitry 50 may adjust the excitation signal (128). For example, by increasing an excitation current, the bio impedance measurement range may become smaller and the top of the bio impedance measurement range may drop. By decreasing an excitation current, the bio impedance measurement range may become larger and the top of the bio impedance measurement range may climb. Processing circuitry 50 may apply the adjusted excitation signal to sensing circuitry 52 (120).

For example, processing circuitry 50 may change the current or the voltage to adjust the bio impedance measurement range. In some examples, processing circuitry 50 may determine the adjusted excitation signal based upon the sensed bio impedance value as discussed above with respect to FIG. 7.

In some examples, processing circuitry 50 may adjust the bio impedance measurement range such that the measured bio impedance value is closer to the center of the adjusted bio impedance measurement range than it was in the bio impedance measurement range prior to the adjustment. In some examples, the measured bio impedance value may not be in a predetermined portion of the adjusted bio impedance measurement range that corresponds to the predetermined portion of the bio impedance measurement range prior to the adjustment as discussed above with respect to FIG. 7. If the sensed bio impedance value was not within the predetermined portion of the bio impedance measurement range (the "NO" path from box 126), processing circuitry 50 may not adjust the excitation signal and may apply the same excitation signal to sensing circuitry 52 (110) the next time processing circuitry 50 attempts to determine a sensed bio impedance value.

This disclosure includes the following non-limiting examples.

Example 1. A device comprising: a plurality of electrodes; sensing circuitry configured to sense a bio impedance; and processing circuitry configured to: apply an excitation signal to the plurality of electrodes via the sensing circuitry; based on the application of the excitation signal, determine a sensed bio impedance value within a bio impedance measurement range; determine whether the sensed bio impedance value is within a predetermined portion of the bio impedance measurement range for a predetermined period of time; and based on the sensed bio impedance value being within the predetermined portion of the bio impedance measurement range for the predetermined period of time, adjust the excitation signal, wherein adjusting the excitation signal adjusts the bio impedance measurement range.

Example 2. The device of example 1, wherein the predetermined portion of the bio impedance measurement range is at least one of an upper boundary limit of the bio impedance measurement range or a lower boundary limit of the bio impedance measurement range.

Example 3. The device of example 1 or example 2, wherein the sensed bio impedance value is within the adjusted bio impedance measurement range and not within a predetermined portion of the adjusted bio impedance measurement range, and wherein the predetermined portion of the adjusted bio impedance measurement range is at least one of a top of the adjusted bio impedance measurement range or a bottom of the adjusted bio impedance measurement range.

Example 4. The device of any combination of examples 1-3, wherein the sensed bio impedance value is closer to a center of the adjusted bio impedance measurement range than the sensed bio impedance value is to the center of the bio impedance measurement range.

Example 5. The device of any combination of examples 1-4, wherein the processing circuitry is configured to adjust the excitation signal by determining an adjusted excitation signal based on the sensed bio impedance value.

Example 6. The device of any combination of examples 1-5, further comprising an accelerometer, wherein the processing circuitry is further configured to: determine whether the device has flipped based on a signal from the accelerometer; and determine whether the sensed bio impedance value is within the predetermined portion of the bio impedance measurement range based on the determination that the device has flipped.

Example 7. The device of any combination of examples 1-6, further comprising communication circuitry configured to transmit the sensed bio impedance value to an external device.

Example 8. The device of any combination of examples 1-7, wherein the processing circuitry is configured to determine whether the sensed bio impedance value is within the predetermined portion of the bio impedance measurement range on a periodic basis.

Example 9. The device of example 8, wherein the periodic basis is daily.

Example 10. The device of any combination of examples 1-9, wherein the processing circuitry is configured to determine whether the sensed bio impedance value is within the predetermined portion of the bio impedance measurement range automatically.

Example 11. A method comprising: applying, by processing circuitry, an excitation signal to a plurality of electrodes via sensing circuitry; determining, by the processing circuitry and based on the application of the excitation signal, a sensed bio impedance value within a bio impedance measurement range; determining, by the processing circuitry, whether the sensed bio impedance value is within a predetermined portion of the bio impedance measurement range for a predetermined period of time; and based on the sensed bio impedance value being within the predetermined portion of the bio impedance measurement range for the predetermined period of time, adjusting the excitation signal, wherein adjusting the excitation signal adjusts the bio impedance measurement range.

Example 12. The method of example 11, wherein the predetermined portion of the bio impedance measurement range is at least one of an upper boundary limit of the bio impedance measurement range or a lower boundary limit of the bio impedance measurement range.

Example 13. The method of example 11 or example 12, wherein the sensed bio impedance value is within the adjusted bio impedance measurement range and not within a predetermined portion of the adjusted bio impedance measurement range, and wherein the predetermined portion of the adjusted bio impedance measurement range is at least one of a top of the adjusted bio impedance measurement range or a bottom of the adjusted bio impedance measurement range.

Example 14. The method of any combination of examples 11-13, wherein the sensed bio impedance value is closer to a center of the adjusted bio impedance measurement range than the sensed bio impedance value is to the center of the bio impedance measurement range.

Example 15. The method of any combination of examples 11-14, wherein adjusting the excitation signal comprises determining an adjusted excitation signal based on the sensed bio impedance value.

Example 16. The method of any combination of examples 11-15, further comprising: determining, by the processing circuitry, whether a device has flipped based on a signal from an accelerometer; and determining, by the processing circuitry, whether the sensed bio impedance value is within the predetermined portion of the bio impedance measurement range based on the determination that the device has flipped.

Example 17. The method of any combination of examples 11-16, further comprising transmitting the sensed bio impedance value to an external device.

Example 18. The method of any combination of examples 11-17, wherein the determining whether the sensed bio impedance value is within the predetermined portion of the bio impedance measurement range is performed on a periodic basis.

Example 19. The method of any combination of examples 11-18, wherein the determining whether the sensed bio impedance value is within the predetermined portion of the bio impedance measurement range is automatic.

Example 20. A non-transitory computer-readable medium comprising instructions for causing one or more processors to: apply an excitation signal to a plurality of electrodes via sensing circuitry; determine, based on the application of the excitation signal, a sensed bio impedance value within a bio impedance measurement range; determine whether the sensed bio impedance value is within a predetermined portion of the bio impedance measurement range for a predetermined period of time; and based on the sensed bio impedance value being within the predetermined portion of the bio impedance measurement range for the predetermined period of time, adjust the excitation signal, wherein adjusting the excitation signal adjusts the bio impedance measurement range.

The techniques described in this disclosure may be implemented, at least in part, in hardware, software, firmware, or any combination thereof. For example, various aspects of the techniques may be implemented within one or more microprocessors, DSPs, ASICs, FPGAs, or any other equivalent integrated or discrete logic QRS circuitry, as well as any combinations of such components, embodied in external devices, such as clinician or patient programmers, stimulators, or other devices. The terms "processor" and "processing circuitry" may generally refer to any of the foregoing logic circuitry, alone or in combination with other logic circuitry, or any other equivalent circuitry, and alone or in combination with other digital or analog circuitry.

For aspects implemented in software, at least some of the functionality ascribed to the systems and devices described in this disclosure may be embodied as instructions on a computer-readable storage medium such as RAM, DRAM, SRAM, magnetic discs, optical discs, flash memories, or forms of EPROM or EEPROM. The instructions may be executed to support one or more aspects of the functionality described in this disclosure.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

Various examples have been described. These and other examples are within the scope of the following claims.

What is claimed is:

1. A device comprising:
   a plurality of electrodes;
   sensing circuitry configured to sense a bio impedance; and
   processing circuitry configured to:
      apply an excitation signal to the plurality of electrodes via the sensing circuitry, wherein applying the excitation signal establishes a bio impedance measurement range within which a bio impedance value is measurable and outside of which the bio impedance value is not measurable as being outside of the bio impedance measurement range, the bio impedance measurement range having an upper boundary limit defining a highest value of the bio impedance measurement range and a lower boundary limit defining a lowest value of the bio impedance measurement range;
      based on the application of the excitation signal, determine a sensed bio impedance value within the bio impedance measurement range;
      determine whether the sensed bio impedance value is within a predetermined portion of the bio impedance measurement range for a predetermined period of time, the predetermined portion of the bio impedance measurement range being smaller than the bio impedance measurement range and comprising either the upper boundary limit or the lower boundary limit; and
      based on a determination of the sensed bio impedance value being within the predetermined portion of the bio impedance measurement range for the predetermined period of time, adjust the excitation signal, wherein adjusting the excitation signal adjusts the bio impedance measurement range to generate an adjusted bio impedance measurement range by changing at least one of the upper boundary limit or the lower boundary limit.

2. The device of claim 1, wherein the predetermined portion of the bio impedance measurement range is the upper boundary limit or the lower boundary limit.

3. The device of claim 1, wherein adjusting the excitation signal adjusts the bio impedance measurement range such that the sensed bio impedance value is within the adjusted bio impedance measurement range and not at a top of the adjusted bio impedance measurement range or at a bottom of the adjusted bio impedance measurement range.

4. The device of claim 1, wherein adjusting the excitation signal adjusts the bio impedance measurement range such that the sensed bio impedance value is closer to a center of the adjusted bio impedance measurement range than the sensed bio impedance value is to a center of the bio impedance measurement range.

5. The device of claim 1, wherein the processing circuitry is configured to adjust the excitation signal by determining an adjusted excitation signal based on the sensed bio impedance value.

6. The device of claim 1, further comprising an accelerometer, wherein the processing circuitry is further configured to:
   determine that the device has flipped based on a signal from the accelerometer, wherein the processing circuitry is configured to determine whether the sensed bio impedance value is within the predetermined portion of the bio impedance measurement range, based on the determination that the device has flipped.

7. The device of claim 1, further comprising communication circuitry configured to transmit the sensed bio impedance value to an external device.

8. The device of claim 1, wherein the processing circuitry is configured to determine whether the sensed bio impedance value is within the predetermined portion of the bio impedance measurement range on a periodic basis.

9. The device of claim 8, wherein the periodic basis is daily.

10. The device of claim 1, wherein the processing circuitry is configured to determine whether the sensed bio impedance value is within the predetermined portion of the bio impedance measurement range automatically.

11. A method comprising:
applying, by processing circuitry, an excitation signal to a plurality of electrodes via sensing circuitry, wherein applying the excitation signal establishes a bio impedance measurement range within which a bio impedance value is measurable and outside of which the bio impedance value is not accurately measurable as being outside of the bio impedance measurement range, the bio impedance measurement range having an upper boundary limit defining a highest value of the bio impedance measurement range and a lower boundary limit defining a lowest value of the bio impedance measurement range;
determining, by the processing circuitry and based on the application of the excitation signal, a sensed bio impedance value within the bio impedance measurement range;
determining, by the processing circuitry, whether the sensed bio impedance value is within a predetermined portion of the bio impedance measurement range for a predetermined period of time, the predetermined portion of the bio impedance measurement range being smaller than the bio impedance measurement range and comprising either the upper boundary limit or the lower boundary limit; and
based on a determination of the sensed bio impedance value being within the predetermined portion of the bio impedance measurement range for the predetermined period of time, adjusting the excitation signal,
wherein adjusting the excitation signal adjusts the bio impedance measurement range by changing at least one of the upper boundary limit or the lower boundary limit.

12. The method of claim 11, wherein the predetermined portion of the bio impedance measurement range is the upper boundary limit or the lower boundary limit.

13. The method of claim 11, wherein adjusting the excitation signal adjusts the bio impedance measurement range such that the sensed bio impedance value is within the adjusted bio impedance measurement range and not at a top of the adjusted bio impedance measurement range or at a bottom of the adjusted bio impedance measurement range.

14. The method of claim 11, wherein adjusting the excitation signal adjusts the bio impedance measurement range such that the sensed bio impedance value is closer to a center of the adjusted bio impedance measurement range than the sensed bio impedance value is to a center of the bio impedance measurement range.

15. The method of claim 11, wherein adjusting the excitation signal comprises determining an adjusted excitation signal based on the sensed bio impedance value.

16. The method of claim 11, further comprising:
determining, by the processing circuitry, that a device has flipped based on a signal from an accelerometer,
wherein determining whether the sensed bio impedance value is within the predetermined portion of the bio impedance measurement range is based on the determination that the device has flipped.

17. The method of claim 11, further comprising transmitting the sensed bio impedance value to an external device.

18. The method of claim 11, wherein the determining whether the sensed bio impedance value is within the predetermined portion of the bio impedance measurement range is performed on a periodic basis.

19. The method of claim 11, wherein the determining whether the sensed bio impedance value is within the predetermined portion of the bio impedance measurement range is automatic.

20. A non-transitory computer-readable medium comprising instructions for causing one or more processors to:
apply an excitation signal to a plurality of electrodes via sensing circuitry, wherein applying the excitation signal establishes a bio impedance measurement range within which a bio impedance value is measurable and outside of which the bio impedance value is not accurately measurable as being outside of the bio impedance measurement range, the bio impedance measurement range having an upper boundary limit defining a highest value of the bio impedance measurement range and a lower boundary limit defining a lowest value of the bio impedance measurement range;
determine, based on the application of the excitation signal, a sensed bio impedance value within the bio impedance measurement range;
determine whether the sensed bio impedance value is within a predetermined portion of the bio impedance measurement range for a predetermined period of time, the predetermined portion of the bio impedance measurement range being smaller than the bio impedance measurement range and comprising either the upper boundary limit or the lower boundary limit; and
based on a determination of the sensed bio impedance value being within the predetermined portion of the bio impedance measurement range for the predetermined period of time, adjust the excitation signal,
wherein adjusting the excitation signal adjusts the bio impedance measurement range by changing at least one of the upper boundary limit or the lower boundary limit.

* * * * *